United States Patent [19]

Mich et al.

[11] Patent Number: 4,657,913

[45] Date of Patent: Apr. 14, 1987

[54] TRIFLUORO- QUINOLINE -3- CARBOXYLIC ACIDS AND THEIR USE AS ANTI-BACTERIAL AGENTS

[75] Inventors: Thomas F. Mich, Ann Arbor; John M. Domagala, Canton; Jeffrey B. Nichols, Ypsilanti, all of Mich.

[73] Assignee: Warner-Lambert Company, Morris Plains, N.J.

[21] Appl. No.: 724,442

[22] Filed: Apr. 18, 1985

[51] Int. Cl.$^4$ ................... A61K 31/47; C07D 215/00
[52] U.S. Cl. .................................. 514/278; 514/312; 546/156; 546/15
[58] Field of Search .................. 546/156, 15, 123; 514/278, 312

[56] References Cited

U.S. PATENT DOCUMENTS

| | | | |
|---|---|---|---|
| 3,907,808 | 9/1975 | Lesher et al. | 546/156 |
| 3,963,736 | 6/1976 | Nakagome et al. | 546/123 |
| 4,292,317 | 8/1981 | Pesson | 546/156 |
| 4,398,029 | 8/1983 | Irikusa et al. | 546/156 |
| 4,448,962 | 5/1984 | Irikura et al. | 546/156 |

FOREIGN PATENT DOCUMENTS

106489  4/1984  European Pat. Off. ............ 546/156

*Primary Examiner*—Henry R. Jiles
*Assistant Examiner*—J. Richter
*Attorney, Agent, or Firm*—Ronald A. Daignault

[57] ABSTRACT

Novel difluoro-naphthyridine- and trifluoroquinoline-carboxylic acids as antibacterial agents are described as well as methods for their manufacture, formulation, and use in treating bacterial infections including the description of certain novel intermediates used in the manufacture of the antibacterial agents.

13 Claims, No Drawings

TRIFLUORO- QUINOLINE -3- CARBOXYLIC ACIDS AND THEIR USE AS ANTI-BACTERIAL AGENTS

BACKGROUND OF THE INVENTION

European Pat. Publication No. 106,489 discloses 6-fluoro-1,4-dihydro-4-oxo-1,8-naphthyridine-3-carboxylic acids and 6,8-difluoro-1,4-dihydro-4-oxoquinoline-3-carboxylic acids as antibacterial agents.

The present invention concerns the corresponding 5,6-difluoronapthyridines and 5,6,8-trifluoroquinolines having valuable antibacterial properties.

SUMMARY OF THE INVENTION

Accordingly, the present invention relates to a compound of the Formula I

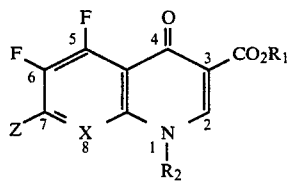

wherein Z is

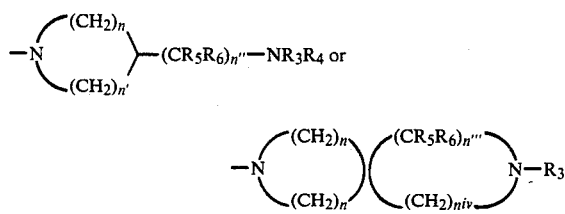

n and n' are each independently 1, 2, 3, or 4, wherein $n+n'$ is a total of 2, 3, 4, or 5; $n''$ is 0, 1, or 2; $n'''$ is 0, 1, or 2; and $n^{iv}$ is 1 to 5; $R_1$ is hydrogen, alkyl having from one to six carbon atoms or a cation; $R_2$ is alkyl having from one to four carbon atoms, vinyl, haloalkyl, or hydroxyalkyl having from two to four carbon atoms, or cycloalkyl having three to six carbon atoms; $R_3$ is hydrogen, alkyl having from one to four carbon atoms or cycloalkyl having three to six carbon atoms; $R_4$ is hydrogen, alkyl from one to four carbon atoms, hydroxyalkyl having two to four carbon atoms, trifluoroethyl or $R_7CO-$ wherein $R_7$ is alkyl having from one to four carbon atoms, or alkoxy having from one to four carbon atoms, $R_5$ is hydrogen, or alkyl having from one to three carbon atoms; $R_6$ is hydrogen or alkyl having from one to three carbon atoms;

Preferred compounds of this invention are those wherein $R_1$ is hydrogen or a pharmaceutically acceptable base salt such as a metal or amine salt.

Other preferred compounds of this invention are those wherein $R_2$ is ethyl, vinyl, 2-fluoroethyl, or cyclopropyl.

Other preferred compounds of this invention are those wherein $R_3$ is hydrogen, methyl, ethyl, or n-propyl, and $R_4$, $R_5$, and $R_6$ are hydrogen.

The most preferred compounds are those wherein X is CF, Z is

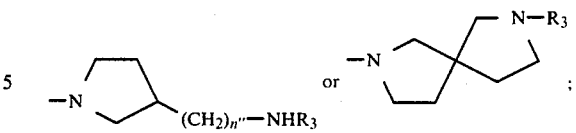

$n''$ is 0 or 1; $R_1$ is hydrogen, $R_2$ is ethyl, vinyl, 2-fluoroethyl, or cyclopropyl, and $R_3$ is hydrogen, methyl, ethyl, 1- or 2-propyl, or a pharmaceutically acceptable acid addition or base salt thereof.

Particularly preferred species of the invention are the compounds having the names: 7-[3-(aminomethyl)-1-pyrrolidinyl]-1-ethyl-5,6-difluoro-1,4-dihydro-4-oxo-1,8-naphthyridine-3-carboxylic acid;

7-[3-(aminomethyl)-1-pyrrolidinyl]-1-ethyl-5,6,8-trifluoro-1,4-dihydro-4-oxo-3-quinolinecarboxylic acid;

7-[3-(aminomethyl)-1-pyrrolidinyl]-5,6,8-trifluoro-1-(2-fluoroethyl)-1,4-dihydro-4-oxo-3-quinolinecarboxylic acid;

7-[3-(aminomethyl)-1-pyrrolidinyl]-5,6,8-trifluoro-1-ethenyl-1,4-dihydro-4-oxo-3-quinolinecarboxylic acid;

1-ethyl-7-[3-[(ethylamino)methyl]-1-pyrrolidinyl]-5,6-difluoro-1,4-dihydro-4-oxo-1,8-naphthyridine-3-carboxylic acid;

1-ethyl-7-[3-[(ethylamino)methyl]-1-pyrrolidinyl]-5,6,8-trifluoro-1,4-dihydro-4-oxo-3-quinolinecarboxylic acid;

7-[3-[(ethylamino)methyl]-1-pyrrolidinyl]-5,6,8-trifluoro-1-(2-fluoroethyl)-1,4-dihydro-4-oxo-3-quinolinecarboxylic acid;

1-ethenyl-7-[3-[(ethylamino)methyl-1-pyrrolidinyl]-5,6,8-trifluoro-1,4-dihydro-4-oxo-3-quinolinecarboxylic acid;

1-ethyl-5,6-difluoro-1,4-dihydro-7-[3-[[(1-methylethyl)amino]methyl]-1-pyrrolidinyl]-4-oxo-1,8-naphthyridine-3-carboxylic acid;

1-ethyl-7-[3-[[(1-methylethyl)amino]methyl]-1-pyrrolidinyl]-5,6,8-trifluoro-1,4-dihydro-4-oxo-3-quinolinecarboxylic acid;

1-ethyl-5,6-difluoro-1,4-dihydro-7-(7-methyl-2,7-diazaspiro[4.4]non-2-yl)-4-oxo-1,8-naphthyridine-3-carboxylic acid;

1-ethyl-5,6,8-trifluoro-1,4-dihydro-7-(7-ethyl-2,7-diazaspiro[4.4]non-2-yl)-4-oxo-3-quinolinecarboxylic acid;

1-ethyl-5,6,8-trifluoro-1,4-dihydro-7-(7-methyl-2,7-diazaspiro[4.4]non-2-yl)-4-oxo-3-quinolinecarboxylic acid;

7-(3-amino-1-pyrrolidinyl)-1-ethyl-5,6,8-trifluoro-1,4-dihydro-4-oxo-3-quinolinecarboxylic acid;

7-[3-(aminomethyl)-1-pyrrolidinyl[-1-cyclopropyl-5,6,8-trifluoro-1,4-dihydro-4-oxo-3-quinolinecarboxylic acid;

1-cyclopropyl-7-[3-(ethylamino)-1-pyrrolidinyl]-5,6,8-trifluoro-1,4-dihydro-4-oxo-3-quinolinecarboxylic acid;

7-[3-amino-1-pyrrolidinyl]-1-cyclopropyl-5,6,8-trifluror-1,4-dihydro-4-oxo-3-quinolinecarboxylic acid;

1-cyclopropyl-7-[3-[(methylamino)methyl]-1-pyrrolidinyl]-5,6,8-trifluoro-1,4-dihydro-4-oxo-3-quinolinecarboxylic acid;

1-cyclopropyl-7-[3-(ethylamino)-1-pyrrolindinyl]-5,6,8-trifluoro-1,4-dihydro-4-oxo-3-quinolinecarboxylic acid;

1-cyclopropyl-5,6,8-trifluoro-1,4-dihydro-7-[[(1-methylethyl)amino]methyl]-1-pyrrolidinyl]-4-oxo-3-quinolinecarboxylic acid;

7-[3-(aminomethyl)-1-pyrrolidinyl]-1-cyclopropyl-1,4-dihydro-5,6-difluoro-4-oxo-1,8-naphthyridine-3-carboxylic acid;

1-cyclopropyl-7-[3-[(ethylamino)methyl]-1-pyrrolidinyl]-1,4-dihydro-5,6-difluoro-4-oxo-1,8-naphthyridine-3-carboxylic acid;

7-[3-amino-1-pyrrolidinyl]-1-cyclopropyl-1,4-dihydro-5,6-difluoro-4-oxo-1,8-naphthyridine-3-carboxylic acid; and the pharmaceutically acceptable acid addition or base salts thereof.

The following process for preparing compounds of the formula

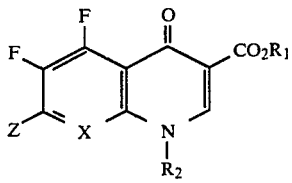

III wherein $R_1$, $R_2$, X, Y, and Z are as defined for Formula I which comprises reacting a compound having the following structural formula

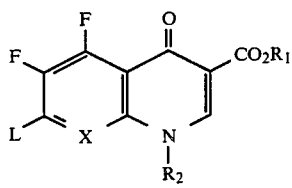

IV with an amine corresponding to the group Z wherein Z is the compound having the structural formula

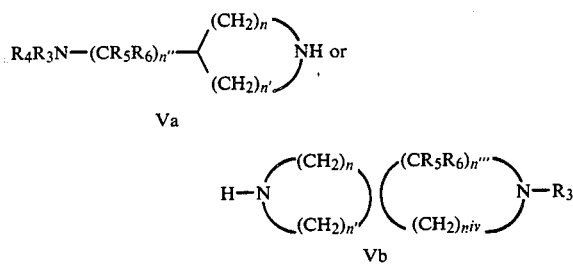

wherein all of the above terms are as defined in Formula I and L is a leaving group which is preferably fluorine or chlorine.

The invention also includes a pharmaceutical composition which comprises an antibacterially effective amount of a compound having structural Formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the invention having the structural Formula III may be readily prepared by treating a corresponding compound having the structural Formula IV with the desired cyclic amine Va or Vb. For purposes of this reaction, the alkylamine substituent of Compound Va or Vb may, if desired, be protected by a group which renders it substantially inert to the reaction conditions. Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, β,β,β-trichloroethoxycarbonyl, β-iodoethoxycarbonyl; aryloxycarbonyl groups such as benzyloxycarbonyl, p-methoxybenzyloxycarbonyl, phenoxycarbonyl; silyl groups such trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound IV and Compound Va or Vb if desired, by procedures known to those skilled in the art. For example, the ethoxycarbonyl group may be removed by acid or base hydrolysis and the trityl group may be removed by hydrogenolysis.

The reaction between the compound of structural Formula IV and a suitably protected compound of Formula Va and Vb, may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of Formula V may be utilized as the acid acceptor.

Convenient solvents for this reaction are non-reactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group $R_4$ may be accomplished either before or after isolating the product, III. Alternatively, the protecting group $R_4$ need not be removed.

The starting compounds having structural Formula IV are known in the art or, if new, may be prepared from known starting materials by standard procedures or by variations thereof.

For example, compounds of Formula IV wherein $R_2$ is other than cycloalkyl may be prepared from tetrafluorobenzene, a commercially available material. Tetrafluorobenzene is first nitrated and the nitro group reduced to amino and, without isolation, reacted with diethyl ethoxymethylenemalonate to afford diethyl 2,3,4,5-tetrafluoroanilinomethylenemalonate which is ring closed by heating to form 5,6,7,8-tetrafluoro-1,4-dihydro-4-oxo-3-quinolinecarboxylic, ethyl ester. Alkylation of the ester and hydrolysis, if desired, gives the appropriate intermediate of Formula IV. An illustration of the above sequence is provided in the Examples.

Alternatively, especially when $R_2$ is cycloalkyl, compounds of Formula IV may be prepared from commercially available pentafluorobenzoic acid. The acid is converted to the benzoylacetic acid ethyl ester via the acid chloride. The intermediate (2) is reacted with acetic anhydride and triethyl orthoformate followed by the appropriate cycloalkylamine, e.g., cyclopropylamine, to give (3) which is ring closed by heating with base. Hydrolysis, if desired, gives the free acid of Formula IV. This method is more specifically described in the Examples and also illustrated by the following flow diagram.

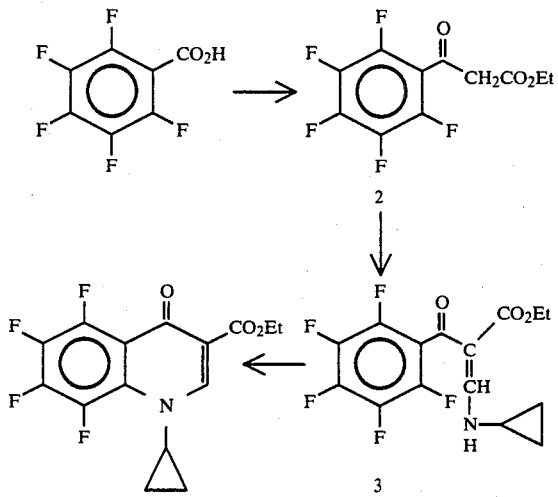

The compounds of the invention having the structural formula Va or Vb are known compounds and may be prepared as described in European Pat. Publication No. 106,489.

The compounds of the invention display antibacterial activity when tested by the microtitration dilution method as described in Heifetz, et al, Antimicr. Agents & Chemoth., 6, 124 (1974), which is incorporated herein by reference.

By use of the above referenced method, the following minimum inhibitory concentration values (MICs in μg/ml) were obtained for representative compounds of the invention.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about three carbon atoms except when specifically stated to be greater than three carbon atoms. Representative of such groups are methyl, ethyl, propyl, isopropyl, and the like.

The cycloalkyl groups contemplated by the invention comprise those having three to six carbons atoms such as cyclopropyl, cyclobutyl, cyclopentyl, and cyclohexyl.

The alkoxy groups contemplated by the invention comprise both straight and branched carbon chains of from one to about four carbon atoms unless otherwise specified. Representative of such groups are methoxy, ethoxy, propoxy, i-propoxy, t-butoxy, and the like.

The term, haloalkyl, is intended to include halogen substituted straight and branched carbon chains of from

| | IN VITRO ANTIBACTERIAL ACTIVITY Minimal Inhibitory Concentration MIC (μg/ml) | | | | |
|---|---|---|---|---|---|
| Organisms | Compound Ex. 1A | Compound Ex. 1B | Compound Ex. 1C | Compound Ex. 1D | Compound Ex. 2A |
| Enterobacter cloacae MA 2646 | 0.8 | 0.8 | 1.6 | 0.4 | 0.4 |
| Escherichia coli Vogel | 0.8 | 0.8 | 0.4 | 0.4 | 0.2 |
| Klebsiella pneumoniae MGH-2 | 0.8 | 1.6 | 0.8 | 0.8 | 0.4 |
| Proteus rettgeri M 1771 | 3.1 | 6.3 | 6.3 | 0.8 | 1.6 |
| Pseudomonas aeruginosa UI-18 | 3.1 | 6.3 | 3.1 | 6.3 | 3.1 |
| Staphlococcus aureus H 228 | 1.6 | 0.8 | 0.8 | 0.4 | 0.2 |
| Staphylococcus aureus UC-76 | 0.8 | 0.2 | 0.05 | 0.013 | 0.025 |
| Streptococcus faecalis MGH-2 | 0.8 | 1.6 | 0.8 | 0.2 | 0.2 |
| Streptococcus pneumoniae SV-1 | ≦0.1 | 0.8 | 0.4 | 0.2 | 0.2 |
| Streptococcus pyogenes C-203 | ≦0.1 | 1.6 | 0.2 | 0.2 | 0.1 |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2-propyl, γ-iodobutyl, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional assymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantites of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

7-[3-(Aminomethyl)-1-pyrrolidinyl]-1-ethyl-5,6,8-trifluoro-1,4-dihydro-4-oxo-3-quinolinecarboxylic acid (A)

To 1.0 g (3.5 mmol) of 1-ethyl-5,6,7,8-tetrafluoro-1,4-dihydro-4-oxo-3-quinolinecarboxylic acid in 20 ml of acetonitrile was added 1.05 g (6.9 mmol) of 1,8-diazobicyclo[5.4.0]undec-7-ene and 0.35 g (3.5 mmol) of 3-pyrrolidinemethanamine and the mixture was stirred at 45° C. for 18 hours, then refluxed one hour. The mixture was cooled, diluted with 50 ml of diethyl ether, and filtered. The solids were washed with ethanol and then diethyl ether to give 1.04 g (82%) of the title compound, mp > 170° C. (decomposition).

In an analogous manner, the following compounds were prepared. (B) 1-Ethyl-5,6,8-trifluoro-1,4-dihydro-7-(7-methyl-2,7-diazaspiro[4.4]nonan-2-yl)-4-oxo-3-quinolinecarboxylic acid, mp 253°–255° C.; (C) 1-Ethyl-5,6,8-trifluoro-1,4-dihydro-7-[3-[(methylamino)methyl]-1-pyrrolidinyl]-4-oxo-3-quinolinecarboxylic acid, mp 225°–227° C.; and (D) 1-Ethyl-7-[3-[(ethylamino)methyl]-1-pyrrolidinyl]-5,6,8-trifluoro-1,4-dihydro-4-oxo-3-quinolinecarboxylic acid, mp 224°–227° C.

EXAMPLE 2

1-Cyclopropyl-7-[3-[(ethylamino)methyl]-1-pyrrolidinyl]-5,6,8-trifluoro-1,4-dihydro-4-oxo-3-quinolinecarboxylic acid (A)

To 1.0 g (3.32 mmol) of 1-cyclopropyl-5,6,7,8-tetrafluoro-1,4-dihydro-4-oxo-3-quinolinecarboxylic acid in 9 ml of acetonitrile was added 0.5 g (one equivalent) of 1,8-diazabicyclo[5.4.0]undec-7-ene and 0.42 g of N-ethyl-3-pyrrolidinemethanamine in 3 ml additional acetonitrile. The mixture was heated at 60° C. for four hours and stirred at 25° C. for 18 hours. The mixture was filtered and the solids washed with diethyl ether to give 1.12 g of the title compound, mp 247°–248° C.

In analogous fashion, the following compounds were prepared. (B) 1-Cyclopropyl-5,6,8-trifluoro-1,4-dihydro-7-[3-quinolinecarboxylic acid; and (C) 7-[3-(Aminomethyl)-1-pyrrolidinyl]-1-cyclopropyl-5,6,8-trifluoro-1,4-dihydro-4-oxo-3-quinolinecarboxylic acid.

EXAMPLE 3

7-[3-Amino-1-pyrrolidinyl]-1-cyclopropyl-5,6,8-trifluoro-1,4-dihydro-4-oxo-3-quinolinecarboxylic acid To 2.0 g (6.64 mmol) of the 1-cyclopropyl-5,6,7,8-tetrafluoro-1,4-dihydro-4-oxo-3-quinolinecarboxylic acid in 10 ml of acetonitrile was added 1.5 g (8.3 mmol) of 3-t-butoxycarbonylaminopyrrolidine and 1.01 g (6.64 mmol) of 1,8-diazabicyclo[5.4.0]undec-7ene. The mixture was stirred overnight and refluxed for two hours. The solids were filtered and washed with ether. They were treated with 5 ml of trifluoroacetic acid and stirred at 25° C. for 1.5 hours. The trifluoroacetic acid was removed and the mixture taken up in water. The pH was adjusted to 7.0 and the solids were filtered and dried to give 2.0 g of the title compound, mp 290°–292° C.

PREPARATION OF THE STARTING MATERIALS

EXAMPLE A 2,3,4,5-Tetrafluoro-1-nitrobenzene

To one liter of concentrated sulfuric acid was added, at 5° C., 100 ml of 1,2,3,4-tetrafluorobenzene. Then a mixture of 100 ml of 70% nitric acid premixed with 200 ml of concentrated sulfuric acid at 0° C. was slowly added. The reaction was stirred at 0° C. for one hour, and then one hour at 25° C. The mixture was poured over ice and extracted with dichloromethane, which was dried and concentrated to give 120 g of a thick residue which was one spot thin layer chromatography. This product was used for the next step without purification.

EXAMPLE B

Diethyl-2,3,4,5-tetrafluoroanilinomethylenemalonate

To 48.6 g (0.25 mol) of 2,3,4,5-tetrafluoro-1-nitrobenzene in 500 ml of 2-propanol was added 3.0 g of Raney Nickel and hydrogen gas at a pressure of 20 psi. After 19 hours, the mixture was vented and filtered directly into a mixture of 58 ml of diethyl ethoxymethylenemalonate and 500 ml of toluene. The toluene was distilled away over three hours and the residue treated with pentane. The solids were filtered to give 62.5 g of the title compound, mp 115°–116° C.

EXAMPLE C 5,6,7,8-Tetrafluoro-1,4-dihydro-4-oxo-3-quinolinecarboxylic, ethyl ester To 700 ml of refluxing dowtherm was added 62.5 g (187 mmol) of diethyl 2,3,4,5-tetrafluoroanilinomethylenemalonate in three portions. After 30 minutes the mixture was cooled, diluted with diethyl ether, and filtered. The solids were washed with diethyl ether to give 40.0 g (74%) of the title compound, mp 282°–283° C.

EXAMPLE D

1-Ethyl-5,6,7,8-tetrafluoro-1,4-dihydro-4-oxo-3-quinolinecarboxylic acid, ethyl ester To 38.5 g (134 mmol) of 5,6,7,8-tetrafluoro-1,4-dihydro-4-oxo-3-quinolinecarboxylic acid, ethyl ester in 700 ml of N,N-dimethylformamide was added 37.15 g (two equivalents) of potassium carbonate and 50 ml (five equivalents) of ethyl iodide. The mixture was brought to 50° C. and stirred vigorously overnight. The solvents were removed and the residue partioned between water and dichloromethane. The dichloromethane was dried (magnesium sulfate) and concentrated. The residue was triturated with diethyl ether to give 30.5 g of material which was recrystallized from ethanol. Filtration gave 23.5 g of the title compound, mp 217°–220° C.

EXAMPLE E

1-Ethyl-5,6,7,8-tetrafluoro-1,4-dihydro-4-oxo-3-quinolinecarboxylic acid

To 20.0 g (63 mmol) of the 1-ethyl-5,6,7,8-tetrafluoro-1,4-dihydro-4-oxo-3-quinoline carboxylic acid, ethyl ester, was added 200 ml of acetic acid and 150 ml of 6N hydrochloric acid in 70 ml of water. The mixture was maintained at 100° C. for two hours. It was cooled, filtered, and washed with diethyl ester, to give 17 g of the title compound, mp 229°–230° C.

EXAMPLE F

Pentafluorobenzoylacetic acid, ethyl ester

To 20.0 g (0.094 mmol) of pentafluorobenzoic acid in 175 ml of dichloromethane was added 9.0 ml (1.1 equivalents) of oxalychloride and three drops of N,N-dimethylformamide. The mixture was allowed to stand overnight and was concentrated. The residue was dissolved in 100 ml of tetrahydrofuran and used without purification for the next step.

To 26 g (two equivalents) of malonic acid half ethyl ester in 600 ml of tetrahydrofuran at −10°−0° C. was added 179 ml (four equivalent) of 2.2N n-butyllithium. When dianion formation was complete, the mixture was cooled to −78° C. and the acid chloride prepared above was slowly added. After addition was complete the mixture was taken to −35° C. and stirred for one hour. It was poured over 94 ml of 2N hydrochloric acid and 200 g of ice. The entire mixture was extracted with dichloromethane and this solution was then extracted with saturated sodium bicarbonate. The dichloromethane was dried and concentrated to give 14.3 g of the title compound isolated as a light yellow oil after column chromatography (toluene:hexane:ether 6:3:1).

EXAMPLE G 2-(Pentafluorobenzoyl)-3-cyclopropylaminoacrylic acid, ethyl ester To 14.0 g (49.6 mmol) of pentafluorobenzoylacetic acid, ethyl ester was added 12.1 g of acetic anhydride and 10.9 g of triethylorthoformate. The mixture was refluxed at 150° C. for 2.2 hours. It was cooled to 80° C. and concentrated for 1.5 hours. The mixture was then cooled to 45° C. and reacted with 2.83 g of cyclopropylamine in 100 ml of 2-propanol. The mixture was stirred overnight and concentrated. The residue was treated with pentane and the solids filtered to give 11.36 g of the title compound as a pale yellow powder, mp 85°–86° C.

EXAMPLE H

1-Cyclopropyl-5,6,7,8-tetrafluoro-1,4-dihydro-4-oxo-3-quinolinecarboxylic acid

To 11.43 g (32.75 mmol) of 2-(pentafluorobenzoyl)-3-cyclopropylaminoacrylic acid, ethyl ester in 250 ml of dioxane was added 4.99 g of 1,8-diazabicyclo[5.4.0]-undec-7-ene at 85° C. The mixture was stirred for two hours and was partitioned between water and dichloromethane. The dichloromethane was washed with 1N hydrochloric acid, was dried, and charcoaled. The mixture was filtered, concentrated, and purified by column chromatography (chloroform:hexane:2-propanol, 6:3:1) to give 2.75 g of product which was dissolved in 40 ml of acetic acid and 8 ml of 2N hydrochloric acid. After two hours at 100° C., 20 ml of water was added. The mixture was cooled and the solids filtered to give 2.5 g of the title compound, mp 179°–180° C.

What is claimed is:

1. A compound of the formula:

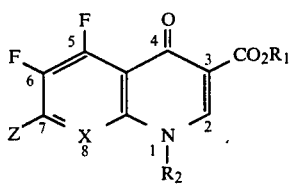

wherein Z is

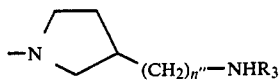

in which n″ is zero or one and $R_3$ is hydrogen, methyl, ethyl, 1- or 2-propyl; or

and $R_3$ is hydrogen, methyl or ethyl; X is CF $R_2$ is ethyl, vinyl, 2-fluoroethyl or cyclopropyl; $R_1$ is hydrogen, or a pharmaceutically acceptable acid addition or base salt thereof.

2. A compound as claimed in claim 1 and being 7-[3-(aminomethyl)-1-pyrrolidinyl]-1-ethyl-5,6,8-trifluoro-1,4-dihydro-4-oxo-3-quinolinecarboxylic acid.

3. A compound as claimed in claim 1 and being 1-ethyl-7-[3-(ethylamino)methyl]-1-pyrrolidinyl]-5,6,8-trifluoro-1,4-dihydro-4-oxo-3quinolinecarboxylic acid.

4. A compound as claimed in claim 1 and being 1-ethyl-5,6,8-trifluoro-1,4-dihydro-7-(7-methyl-2,7-diazaspiro[4.4]non-2-yl)-4-oxo-3-quinolinecarboxylic acid.

5. A compound as claimed in claim 1 and being 7-[3-(aminomethyl)-1-pyrrolidinyl]-1-cyclopropyl-5,6,8-trifluoro-1,4-dihydro-4-oxo-3-quinolinecarboxylic acid.

6. A compound as claimed in claim 1 and being 1-cyclopropyl-7-[3-[(ethylamino)methyl]-1-pyrrolidinyl]-5,6,8-trifluoro-1,4-dihydro-4-oxo-3-quinolinecarboxylic acid.

7. A compound as claimed in claim 1 and being 7-[3-amino-1-pyrrolidinyl]-1-cyclopropyl-5,6,8-trifluoro-1,4-dihydro-4-oxo-3-quinolinecarboxylic acid.

8. A compound as claimed in claim 1 and being 1-cyclopropyl-7-[3-[(methylamino)methyl]-1pyrrolidinyl]-5,6,8-trifluoro-1,4-dihydro-4-oxo-3-quinolinecarboxylic acid.

9. A compound as claimed in claim 1 and being 1-cyclopropyl-7-[3-(ethylamino)-1-pyrrolidinyl]-5,6,8-trifluoro-1,4-dihydro-4-oxo-3-quinolinecarboxylic acid.

10. A compound as claimed in claim 1 and being 1-cyclopropyl-5,6,8-difluoro-1,4-dihydro-7-[3-[[(1-methylethyl)amino]methyl]-1-pyrrolidinyl]-4-oxo-3-quinolinecarboxylic acid.

11. A compound as claimed in claim 1 and being 7-(3-amino-1-pyrrolidinyl)-1-ethyl-5,6,8-trifluoro-1,4-dihydro-4-oxo-3-quinolinecarboxylic acid.

12. An antibacterial composition comprising an antibacterially effective amount of a compound as claimed in claim 1 together with a pharmaceutically acceptable carrier.

13. The method of treating bacterial infections in mammals which comprises administering to said mammal an antibacterial composition as claimed in claim 12.

* * * * *